United States Patent
Li

(10) Patent No.: US 9,427,297 B2
(45) Date of Patent: Aug. 30, 2016

(54) SURGICAL MESHES WITH RADIOPAQUE COATINGS

(75) Inventor: Jianmin Li, Lexington, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1875 days.

(21) Appl. No.: 12/437,031

(22) Filed: May 7, 2009

(65) Prior Publication Data

US 2009/0281558 A1  Nov. 12, 2009

Related U.S. Application Data

(60) Provisional application No. 61/051,701, filed on May 9, 2008.

(51) Int. Cl.
| *A61F 2/00* | (2006.01) |
| *A61L 31/10* | (2006.01) |
| *A61L 31/16* | (2006.01) |
| *A61L 31/18* | (2006.01) |

(52) U.S. Cl.
CPC ............ *A61F 2/0063* (2013.01); *A61F 2/0045* (2013.01); *A61L 31/10* (2013.01); *A61L 31/16* (2013.01); *A61L 31/18* (2013.01); *A61F 2250/0098* (2013.01); *A61L 2300/104* (2013.01); *A61L 2300/402* (2013.01); *A61L 2300/406* (2013.01); *A61L 2300/43* (2013.01)

(58) Field of Classification Search
CPC .................................................. A61F 2/0063
USPC ................. 606/151, 213, 214, 215; 623/23.72–23.76; 424/423, 618; 427/2.1, 2.24, 2.31
See application file for complete search history.

(56) References Cited

U.S. PATENT DOCUMENTS

| 4,902,503 | A | 2/1990 | Umemura et al. |
| 5,049,140 | A | 9/1991 | Brenner et al. |
| 5,505,695 | A | 4/1996 | Eplett, Jr. |
| 5,928,174 | A | 7/1999 | Gibbins |
| 6,277,108 | B1 | 8/2001 | McBroom et al. |
| 6,355,858 | B1 | 3/2002 | Gibbins |
| 6,605,751 | B1 | 8/2003 | Gibbins et al. |
| 6,897,349 | B2 | 5/2005 | Gibbins et al. |
| 2004/0106845 | A1* | 6/2004 | Anderson et al. ............... 600/30 |
| 2004/0122509 | A1* | 6/2004 | Brodeur ....................... 623/1.34 |
| 2004/0147618 | A1 | 7/2004 | Lee et al. |
| 2005/0025800 | A1 | 2/2005 | Tan |
| 2005/0064176 | A1* | 3/2005 | Terry ............................ 428/323 |
| 2005/0078158 | A1 | 4/2005 | Magdassi et al. |

(Continued)

FOREIGN PATENT DOCUMENTS

WO    WO200074633 A2    12/2000

OTHER PUBLICATIONS

U.S. Appl. No. 12/437,099, Li.

(Continued)

*Primary Examiner* — Thomas McEvoy

(57) ABSTRACT

According to an aspect of the present invention, implantable medical articles are provided, which comprise a surgical mesh that is at least partially covered with a coating that comprises a radiopaque material such as a metal or a metallic compound. The radiopaque material is present in the coating in an amount such that the coated portions of the mesh are visible using radiographic imaging techniques. Other aspects of the invention pertain to methods of making and using such medical articles.

22 Claims, 1 Drawing Sheet

(56) References Cited

U.S. PATENT DOCUMENTS

| | | | |
|---|---|---|---|
| 2006/0189113 A1 | 8/2006 | Vanheusden et al. | |
| 2006/0195013 A1 | 8/2006 | Gellman et al. | |
| 2006/0210700 A1 | 9/2006 | Lachner | |
| 2006/0254387 A1 | 11/2006 | Lee et al. | |
| 2006/0264698 A1* | 11/2006 | Kondonis et al. | 600/37 |
| 2007/0003603 A1 | 1/2007 | Karandikar et al. | |
| 2007/0018140 A1 | 1/2007 | Lee et al. | |
| 2007/0034052 A1 | 2/2007 | Vanheusden et al. | |
| 2007/0135751 A1* | 6/2007 | DiCarlo et al. | 604/19 |

OTHER PUBLICATIONS

Fred E. Govier et al., "Pubocaginal slings: a review of the technical variables," Curr. Opin Urol. 2001,11, pp. 405-410.

John Klutke et al., "The promise of tension-free vaginal tape for female SUI," Contemporary Urol., Oct. 2000, pp. 59-60, 65-66, 69-70, 73.

"NanoDynamics is Commercializing Nanosilver for Electronics and Healthcare," Apr. 4, 1996, 2 pp. Downloaded from www.ndmaterials.com on Sep. 13, 2007.

F. Furno et al., "Silver nanoparticles and polymeric medical devices: a new approach to prevention of infection?" Journal of Antimicrobial Chemotherapy, 2004, 54, pp. 1019-1024.

Bruce L. Gibbins, "SilvaGard™ Technology Summary," 2005, 8 pp.

Bruce L. Gibbins, "Novel Antimicrobial Treatment," Jul. 2005, 5 pp.

M. Powers, "Antimicrobial silver nanoparticles eliminate biofilm formation on medical devices," NanoBiotech News, Aug. 10, vol. 3, No. 30, Aug. 10, 2005, 2 pp.

Products | Materials | Metals | Silver, 2007, Nanodynamics®, 2 pp., downloaded from www.ndmaterials.com on Dec. 21, 2007.

SST, Products, "Radiopaque Polypropylene Monofilament Mesh," downloaded from http:/www.soveta.it/Precut.htm on Oct. 14, 2007, 1 p.

* cited by examiner

SURGICAL MESHES WITH RADIOPAQUE COATINGS

STATEMENT OF RELATED APPLICATIONS

This application claims the benefit of U.S. Provisional Patent Application Ser. No. 61/051,701, filed May 9, 2008, entitled "Surgical Meshes With Radiopaque Coatings", which is incorporated in its entirety by reference herein.

FIELD OF THE INVENTION

The present invention relates generally to medical articles, and more particularly to surgical meshes that are visible using radiographic imaging techniques.

BACKGROUND OF THE INVENTION

Urinary incontinence affects millions of men and women of all ages in the United States. Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results. A popular treatment of SUI is via the use of a surgical mesh, commonly referred to as a sling, which is permanently placed under a patient's bladder neck or mid-urethra to provide a urethral platform. Placement of the sling limits the endopelvic fascia drop, while providing compression to the urethral sphincter to improve coaptation. Further information regarding sling procedures may be found, for example, in the following: Fred E. Govier et al., "Pubocaginal slings: a review of the technical variables," *Curr. Opin Urol.* 11:405-410, 2001, John Klutke and Carl Klutke, "The promise of tension-free vaginal tape for female SUI," *Contemporary Urol.* pp. 59-73, October 2000; and PCT Patent Publication No. WO 00/74633 A2: "Method and Apparatus for Adjusting Flexible Areal Polymer Implants."

Pelvic floor (pelvic support) disorders involve a dropping down (prolapse) of the bladder, rectum, or uterus caused by weakness of or injury to the ligaments, connective tissue, and muscles of the pelvis. The different types of pelvic floor disorders are named according to the organ affected. For example, a rectocele develops when the rectum drops down and protrudes into the back wall of the vagina. An enterocele develops when the small intestine and the lining of the abdominal cavity (peritoneum) bulge downward between the uterus and the rectum or, if the uterus has been removed, between the bladder and the rectum. A cystocele develops when the bladder drops down and protrudes into the front wall of the vagina. In prolapse of the uterus (procidentia), the uterus drops down into the vagina. See, e.g., The Merck Manuals Online Medical Library, Home Edition, "Pelvic Floor Disorders," www.merck.com. As with SUI, pelvic floor disorders are commonly treated by implanting a surgical mesh within the patient's pelvis to support the organ or organs that require support.

Further uses of surgically implantable meshes include meshes for hernia repair (e.g., meshes for inguinal hernia, hiatus hernia, etc.), meshes for thoracic wall defects, breast support meshes and various other soft-tissue surgical mesh support devices, including meshes for cosmetic and reconstructive surgery, among others.

Surgical meshes are commonly formed from synthetic and biologic materials, which are not visible using radiographic imaging techniques.

SUMMARY OF THE INVENTION

According to an aspect of the present invention, implantable medical articles are provided, which comprise a surgical mesh that is at least partially covered with a coating that comprises a radiopaque material such as a metal or a metallic compound. The radiopaque material is present in the coating in an amount such that the coated portions of the mesh are visible using radiographic imaging techniques.

Other aspects of the invention pertain to methods of making and using such medical articles.

An advantage of the present invention is that surgical meshes are provided which are observable using radiographic imaging techniques, for example, during implantation procedures or during follow-up examinations after implantation.

These and other aspects, embodiments and advantages of the present invention will become immediately apparent to those of ordinary skill in the art upon review of the Detailed Description and any claims to follow.

DETAILED DESCRIPTION OF THE INVENTION

Figure 1:
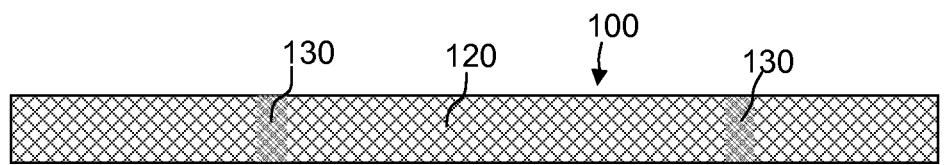
FIG. 1 is a schematic top view of a surgical mesh, in accordance with an embodiment of the invention.

A more complete understanding of the present invention is available by reference to the following detailed description of numerous aspects and embodiments of the invention. The detailed description of the invention which follows is intended to illustrate but not limit the invention.

According to an aspect of the present invention, implantable medical articles are provided, which comprise a surgical mesh that is at least partially covered with a coating that comprises a radiopaque material such as a metal or a metallic compound. The radiopaque material is present in the coating in an amount such that the coated portions of the mesh are visible under radiographic imaging. For example, in some embodiments, the radiopaque material may be present in the coating in an amount such that the coated portions of the mesh are visible under x-ray fluoroscopy. Examples of radiopaque materials that are suitable for use in the coatings of the invention include metals such as silver, barium, and other heavy metals, as well as their various compounds (e.g., metal salts).

In certain embodiments, the coating is also visible by imaging techniques that are not based on ionizing radiation, for example, ultrasonic imaging.

Coatings in accordance with the invention typically contain 10 wt % or more of one or more radiopaque materials (e.g. from 10 wt % to 25 wt % to 40 wt % to 50 wt % to 60 wt % to 70 wt % to 80 wt % to 90 wt % to 95 wt % to 97 wt % to 99 wt % or more).

Coatings in accordance with the invention may be discontinuous in some embodiments, providing only partial coverage of the underlying mesh. For example, coatings in accordance with the invention may form certain patterns to indicate the orientation of the mesh.

In some embodiments, the coatings of the invention comprise silver or a silver salt. Such coatings are desirable in that, in addition to providing radiopacity, the silver can also provide an antimicrobial effect. In this regard, it is known that certain metals such as silver, gold, copper and zinc as well as compounds thereof exert an antimicrobial effect on a wide spectrum of microorganisms, including various bacteria and fungi, at very low metal ion concentrations. This effect is called an oligodynamic effect. Moreover, medical devices have been produced which take advantage of this effect. See, e.g., U.S. Pat. No. 4,902,503.

Thus, in embodiments where the radiopaque material comprises silver, the release of silver ions may form an antimicrobial zone which inhibits or prevents the growth of bacteria, which inhibits or prevents the migration of bacteria along the mesh, or both. In these embodiments, the coatings of the invention may reduce infection, as well as providing visibility under radiographic imaging.

For radiopacity, an amount of silver is significantly higher than that required for antimicrobial activity. In certain embodiments, the silver may be present in the coating in an amount that is at least 1 mg/mm$^2$ and ranging, for example, from 1 to 100 mg/mm$^2$, where the area is the fiber surface area.

In some embodiments, the coatings of the invention comprise metallic particles.

Metallic particles for the practice of the invention may range widely in size. For example, the metallic particles may have at least one dimension (e.g., the thickness) that is 100 microns or less. For example, at least one dimension may range, for example, from 100 microns to 50 microns to 25 microns to 10 microns to 5 microns to 2 microns to 1 micron to 1000 nm to 500 nm to 250 nm to 100 nm to 50 nm to 25 nm to 10 nm or less. As used herein, "nanoparticles" have at least one dimension that is less than 1000 nm (e.g., at least the diameter is less than 1000 nm for a nanofiber or nanotube, at least the thickness is less than 1000 nm for a nanoplate or nanoribbon, at least the diameter is less than 1000 nm for a nanosphere, etc.). In some embodiments, nanoparticles are employed in which all dimensions (e.g., length, width, height, diameter, etc.) are less than 1000 nm.

Metallic particles used in the present invention contain one or more metals, typically 50 wt % or more of one or more metals (e.g. from 50 wt % to 60 wt % to 70 wt % to 80 wt % to 90 wt % to 95 wt % to 97 wt % to 99 wt % or more).

As noted above, silver is known to have good antimicrobial properties. Due to their small size, silver nanoparticles have increased surface area per unit mass relative to larger particles, which leads to higher release rates of silver species (e.g., ions) than those exhibited by larger particles.

Coatings in accordance with the invention may also comprise materials in addition to one or more radiopaque materials. Such additional materials may be selected, for example, from matrix materials (e.g., an organic material such as a polymer, etc.) and therapeutic agents.

Examples of therapeutic agents include corticosteroids, narcotic and non-narcotic analgesics, local anesthetic agents, antibiotics and combinations thereof, among many others.

Examples of matrix materials include polymers (biostable or biodisintegrable) and other organic materials. Organic matrix materials may be selected, for example, from suitable materials containing one or more of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as poly(styrene-b-isobutylene-b-styrene) or SIBS, which is described, for instance, in U.S. Pat. No. 6,545,097 to Pinchuk et al.), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, and glycosaminoglycans such as hyaluronic acid; as well as blends and further copolymers of the above.

In various embodiments, the coatings of the invention are patterned coatings. For example, coatings may be in the form of indicator marks for determining the orientation and/or position of the surgical meshes during implantation. Such indicator marks may also be used to determine the orientation and/or position of the surgical meshes at the time of a follow-up examination. For example, such marks will enable a physician to monitor changes in the location (e.g., due to migration) or dimension (e.g., due to shrinkage) of the meshes.

Moreover, where the coatings contain antimicrobial metals such as silver, such indicator marks can also, for example, act to block microbial migration/advancement along the surface of the meshes.

Surgically implantable meshes in accordance with the invention include, for example, meshes for pelvic floor repair, meshes for renal pelvis repair, urethral slings, vaginal slings, hernia meshes (e.g., meshes for inguinal hernia, hiatus hernia, etc.), meshes for thoracic wall defects, breast support meshes and various other soft-tissue surgical mesh support devices, including meshes for cosmetic and reconstructive surgery, among others.

Surgical meshes in accordance with the present invention include synthetic meshes and biologic meshes (e.g., xenograft and allograft meshes, including decellularized dermis, etc.)

Surgical meshes in accordance with the present invention may be in the form of ribbons, sheets, and other more complex sheet-based shapes.

Surgical meshes in accordance with the present invention may be formed using one or more filaments (e.g., fibers, fibrils, threads, yarns, etc.). Thus, surgical meshes in accordance with the present invention include monofilament and multifilament meshes. Surgical meshes in accordance with the present invention include woven meshes and non-woven meshes (including knitted meshes, felt meshes, and spunbound meshes, among others). Surgical meshes in accordance with the present invention include meshes having small pores (less than 1 mm) and those having large pores (greater than or equal to 1 mm).

Filaments for forming meshes in accordance with the present invention include those formed from various biostable or biodisintegrable polymers, which may be selected from the various biostable and biodisintegrable polymers listed above, among others, as well as biologics. A few specific example of filaments include synthetic filaments formed from (a) polyolefins, including homopolymers and copolymers of C1-C8 alkenes, for example, polypropylene, (b) fluoropolymers, including homopolymers and copolymers of C1-C8 alkenes in which one or more hydrogen atoms are substituted with fluorine, for example, polytetrafluoroethylene and polyvinylidene fluoride, and (c) polyesters, including, for example, polyethylene terephthalate, among other polymers.

As noted above, a popular treatment of stress urinary incontinence (SUI) is via the use of a surgical mesh, commonly referred to as a sling, which is placed under a patient's bladder neck or mid-urethra to provide a urethral platform. Placement of the sling limits the endopelvic fascia drop, while providing compression to the urethral sphincter to improve coaptation.

There is schematically illustrated in FIG. 1, a mesh 100, such as a urethral sling, which includes a mesh material 110 and two regions 130 wherein the mesh is coated with a coating in accordance with the invention. The coated regions 130 may act as markers for radiographic visualization by a physician and may also act as barriers to microbial advancement along the length of the mesh 100 in some embodiments (e.g., where an antimicrobial metal such as silver is employed).

As previously noted, pelvic floor (pelvic support) disorders involve a dropping down (prolapse) of the bladder, rectum, or uterus caused by weakness of or injury to the ligaments, connective tissue, and muscles of the pelvis. As with SUI, treatment of pelvic floor disorders are commonly treated by implanting a surgical mesh within the patient's pelvis to support the organ or organs that require support.

Figure 2:
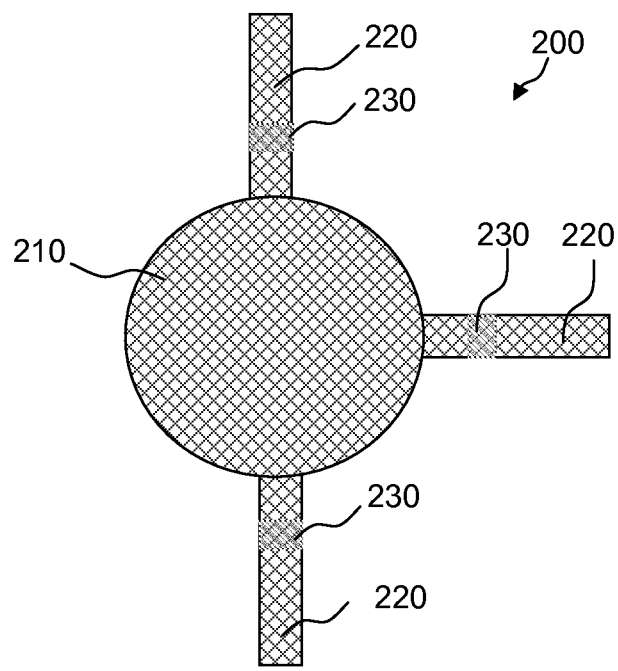
FIG. 2 is a schematic top view of a surgical mesh, in accordance with another embodiment of the invention.

In accordance with another embodiment of the invention, there is schematically illustrated in FIG. 2, a mesh 200, for example, a pelvic floor repair mesh, having a central portion 210 and a plurality of arms 220 that emanate from the central portion 210. As used herein an "arm" is an elongated mesh component whose length is greater than its width. (Thus, surgical sling 100 of FIG. 1 can be thought of as a single-arm device.) Each arm 220 is provided with a region 230 wherein the mesh is coated with a coating in accordance with the invention. As above, the coated regions 230 may act as radiopaque markers for visualization by the physician, and they may also act as barriers to microbial advancement along the length of the arms 220 in some embodiments.

Figure 3:
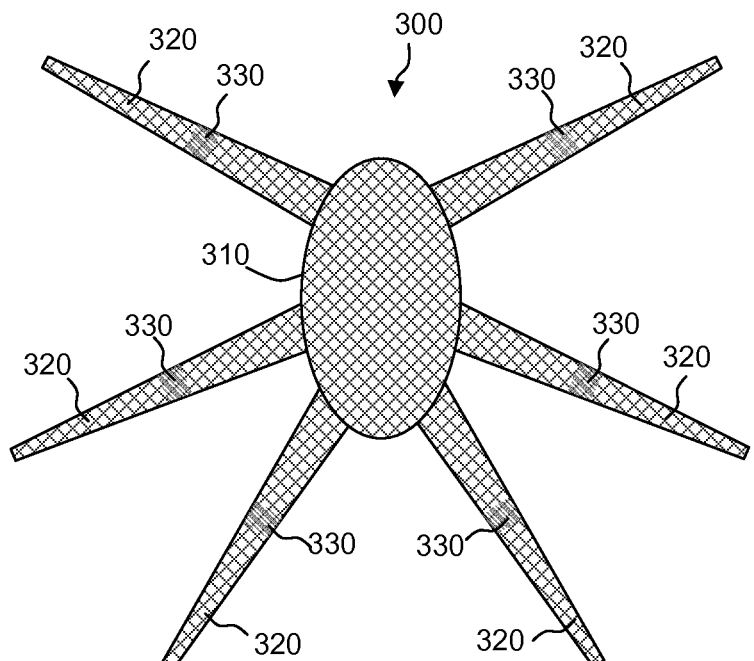
FIG. 3 is a schematic top view of a surgical mesh, in accordance with yet another embodiment of the invention.

Although the mesh of FIG. 2 has three rectangular arms and a circular body portion, other body and arm shapes and other numbers of arms may be used (e.g., 2, 4, 5, 6, 7, 8, etc.). As one specific variation, FIG. 3 illustrates a mesh 300 having a non-circular (oval) central body portion 310 and six non-rectangular (trapezoidal) arms 320, among near limitless other possibilities. As above, each arm 320 is provided with a region 330 wherein the mesh is coated with a coating in accordance with the invention, which coated regions 330 may act as radiopaque markers for visualization by the physician and may also act as barriers to microbial advancement along the length of the arms 320 in some embodiments. Moreover, although not shown, the coated regions may be provided on some, but not all, of the arms, multiple coated regions may be provided on a single arm, and so forth.

Other aspects of the invention pertain to methods by which surgical meshes may be provided with coatings in accordance with the invention. For example, in some embodiments, coatings may be formed using metal deposition techniques such as physical vapor deposition or electrochemical deposition. A suitable mask may be provided over the mesh to create coatings with a desired pattern in some embodiments.

In some embodiments, coatings in accordance with the invention are applied in the form of a fluid (e.g., a solution, dispersion, melt, etc.) using a suitable application technique, which may be selected, for example, from dipping techniques, spraying techniques, spin coating techniques, web coating techniques, techniques involving coating via mechanical suspension including air suspension, electrostatic techniques, techniques in which fluid is selectively applied to only to certain regions of the mesh, for example, through the use of a suitable application device such as a sprayer, brush, roller, pen, or printer (e.g., screen printing device, ink jet printer, etc.).

In certain embodiments, coatings in accordance with the invention are formed from fluids that comprise at least one type of metallic particle, at least one type of polymer, and any additional agent such as a therapeutic agent. For example, solvent-based techniques may be used to form coatings in some embodiments. Using these techniques, coatings can be formed, for instance, by (a) applying to a surgical mesh a solution or dispersion that contains one or more solvent species, one or more polymers, one or more types of metallic particles and, optionally, one or more additional agents, and (b) subsequently removing the solvent species.

As another example, where the coatings of the invention contain one or more polymers having thermoplastic characteristics, thermoplastic processing techniques may be used to form the coatings. Using these techniques, coatings can be formed, for instance, by (a) applying to a surgical mesh a melt that contains one or more polymers, one or more types of metallic particles and, optionally, one or more additional agents, and (b) subsequently cooling the melt.

Various aspects of the invention relating to the above are enumerated in the following paragraphs:

Aspect 1. An implantable medical article comprising a surgical mesh that is at least partially covered with a coating that comprises a metal, wherein the metal is present in the coating in an amount such that the coating is visible under radiographic imaging.

Aspect 2. The medical article of aspect 1, wherein the metal is present in the coating in an amount such that the coating is visible under x-ray fluoroscopy.

Aspect 3. The medical article of aspect 1, wherein the coating comprises silver.

Aspect 4. The medical article of aspect 1, wherein the silver is present in an amount of at least 10 wt %.

Aspect 5. The medical article of aspect 1, wherein the coating comprises particles that comprise the metal.

Aspect 6. The medical article of aspect 1, wherein the coating comprises particles that comprise silver.

Aspect 7. The medical article of aspect 1, wherein the coating comprises metallic particles and a polymer.

Aspect 8. The medical article of aspect 7, wherein the polymer is a biodisintegrable polymer.

Aspect 9. The medical article of aspect 7, wherein the polymer is a biostable polymer.

Aspect 10. The medical article of aspect 7, wherein the polymer is selected from poly(styrene-co-isobutylene), ethylene-vinylacetate copolymer and polypropylene.

Aspect 11. The medical article of aspect 1, wherein the surgical mesh is a synthetic mesh.

Aspect 12. The medical article of aspect 11, wherein the synthetic mesh comprises a polymer selected from polyolefins, fluoropolymers, and polyesters.

Aspect 13. The medical article of aspect 1, wherein the surgical mesh is a biologic mesh.

Aspect 14. The medical article of aspect 13, wherein the biologic mesh is selected from a xenograft mesh and an allograft mesh.

Aspect 15. The medical article of aspect 1, wherein the coating comprises a marker that allows in vivo radiographic visualization of the size of the device, the position of the device, or both.

Aspect 16. The medical article of aspect 1, wherein the coating comprises a plurality of markers that allow in vivo radiographic visualization of the size of the device, the position of the device, or both.

Aspect 17. The medical article of aspect 1, wherein the surgical mesh comprises an arm.

Aspect 18. The medical article of aspect 17, wherein the coating partially covers the arm.

Aspect 19. The medical article of aspect 1, wherein the medical article comprises a plurality of arms.

Aspect 20. The medical article of aspect 19, wherein the coating partially covers each arm.

Aspect 21. The medical article of aspect 1, wherein the medical article further comprises an agent selected from a corticosteroid, a narcotic analgesic, a non-narcotic analgesic, a local anesthetic agent, an antibiotic, and a combination of the forgoing.

Aspect 22. A method of forming the medical article of aspect 1, comprising applying a liquid formulation that comprises the metal to the surgical mesh.

Aspect 23. The method of aspect 22, wherein the liquid formulation comprises a polymer and particles that comprise the metal.

Aspect 24. The method of aspect 23, wherein the liquid formulation further comprises one or more solvent species.

Aspect 25. The method of aspect 22, wherein the liquid formulation is applied using a printing technique.

Aspect 26. An implantable medical article comprising a surgical mesh that is at least partially covered with a coating that comprises silver, wherein the silver is present in the coating in an amount such that the coating is visible under radiographic imaging and wherein the silver ions are released over time into the surrounding tissue in a concentration sufficient to function as antimicrobial agent.

EXAMPLE 25 grams metallic silver nanoparticles (NanoDynamics, Inc. (http://www.nanodynamics.com/) are dispersed into 100 mL 5% SIBS solution in DMF. A suitable colorant is added if needed. The solution may be painted onto a surgical mesh with a brush or sprayed on a surgical mesh using a stencil as mask. Using different polymeric materials as carriers will lead to different release properties for the silver nanoparticles.

Although various embodiments are specifically illustrated and described herein, it will be appreciated that modifications and variations of the present invention are covered by the above teachings and are within the purview of any appended claims without departing from the spirit and intended scope of the invention.

The invention claimed is:

1. An implantable medical article comprising a surgical mesh that is partially covered with a coating that comprises a metal, wherein the metal is present in the coating in an amount such that the coating is visible under radiographic imaging, and wherein said coating comprises a plurality of indicator marks that allow in vivo radiographic visualization of the orientation and/or position of the mesh during and after implantation, wherein said coating comprises silver in an amount of at least 1 mg per $mm^2$ of fiber surface area.

2. The medical article of claim 1, wherein said metal is present in the coating in an amount such that the coating is visible under x-ray fluoroscopy.

3. The medical article of claim 1, wherein said coating comprises silver.

4. The medical article of claim 1, wherein said silver is present in an amount of at least 10 wt %.

5. The medical article of claim 1, wherein said coating comprises particles that comprise said metal.

6. The medical article of claim 1, wherein said coating comprises particles that comprise silver.

7. The medical article of claim 1, wherein said coating comprises metallic particles and a polymer.

8. The medical article of claim 7, wherein said polymer is a biodisintegrable polymer.

9. The medical article of claim 7, wherein said polymer is a biostable polymer.

10. The medical article of claim 7, wherein said polymer is selected from poly(styrene-co-isobutylene), ethylene-vinylacetate copolymer and polypropylene.

11. The medical article of claim 1, wherein said surgical mesh is a synthetic mesh.

12. The medical article of claim 11, wherein said synthetic mesh comprises a polymer selected from polyolefins, fluoropolymers, and polyesters.

13. The medical article of claim 1, wherein said surgical mesh is a biologic mesh.

14. The medical article of claim 13, wherein said biologic mesh is selected from a xenograft mesh and an allograft mesh.

15. The medical article of claim 1, wherein said surgical mesh comprises an arm.

16. The medical article of claim 15, wherein said arm comprises one or more of said indicator marks.

17. The medical article of claim 1, wherein said medical article comprises a central body and a plurality of arms.

18. The medical article of claim 17, wherein each arm comprises an indicator mark.

19. The medical article of claim 17, wherein an arm is provided with multiple indicator marks.

20. The medical article of claim 17, wherein the indicator mark does not extend along the entire length of the arm.

21. The medical article of claim 1, wherein said medical article further comprises an agent selected from a corticosteroid, a narcotic analgesic, a non-narcotic analgesic, a local anesthetic agent, an antibiotic, and a combination of the forgoing.

22. An implantable medical article comprising a surgical mesh that is partially covered with a coating that comprises silver, wherein the silver is present in the coating in an amount of at least 1 mg per $mm^2$ of fiber surface area, wherein the coating is visible under radiographic imaging and wherein the silver ions are released over time into the surrounding tissue in a concentration sufficient to function as antimicrobial agent.

* * * * *